(12) United States Patent
Heeps et al.

(10) Patent No.: US 8,641,730 B2
(45) Date of Patent: Feb. 4, 2014

(54) LOCAL BIOMECHANICAL AND/OR ANTIMICROBIAL LIGATION DEVICE

(75) Inventors: Andrew Heeps, Kensington, CT (US); Jon Wojculewicz, Bristol, CT (US)

(73) Assignee: Covidien LP, Mansfield, MA (US)

( * ) Notice: Subject to any disclaimer, the term of this patent is extended or adjusted under 35 U.S.C. 154(b) by 296 days.

(21) Appl. No.: 12/542,883

(22) Filed: Aug. 18, 2009

(65) Prior Publication Data
US 2011/0046647 A1   Feb. 24, 2011

(51) Int. Cl.
*A61B 17/122* (2006.01)
*A61B 17/064* (2006.01)
*A61B 17/08* (2006.01)
*A61M 5/00* (2006.01)

(52) U.S. Cl.
USPC ............ 606/157; 606/151; 606/158; 606/220

(58) Field of Classification Search
USPC ........... 606/75, 119–120, 142–143, 151–158, 606/213, 215, 219–220, 280, 289, 291; 227/8, 16, 19, 901–902; 24/114.6, 304; 604/415; 411/511–512, 520–530; 424/422
See application file for complete search history.

(56) References Cited

U.S. PATENT DOCUMENTS

| | | | | |
|---|---|---|---|---|
| 3,744,495 A * | 7/1973 | Johnson | | 606/142 |
| 4,402,445 A * | 9/1983 | Green | | 227/19 |
| 4,490,326 A | 12/1984 | Beroff | | |
| 4,531,522 A * | 7/1985 | Bedi et al. | | 606/220 |
| 4,532,926 A * | 8/1985 | O'Holla | | 606/220 |
| 4,534,350 A * | 8/1985 | Golden et al. | | 606/220 |
| 4,545,377 A * | 10/1985 | Cerwin et al. | | 606/158 |
| 4,627,437 A * | 12/1986 | Bedi et al. | | 606/220 |
| 4,646,741 A * | 3/1987 | Smith | | 606/220 |
| 4,667,674 A * | 5/1987 | Korthoff et al. | | 606/220 |
| 4,671,280 A * | 6/1987 | Dorband et al. | | 606/220 |
| 4,693,248 A * | 9/1987 | Failla | | 606/220 |
| 4,890,613 A | 1/1990 | Golden | | |
| 5,250,058 A * | 10/1993 | Miller et al. | | 606/154 |
| 5,258,012 A | 11/1993 | Luscombe et al. | | |
| 5,282,829 A | 2/1994 | Hermes | | |
| 5,306,283 A | 4/1994 | Conners | | |
| 5,584,835 A * | 12/1996 | Greenfield | | 606/232 |
| 5,620,452 A * | 4/1997 | Yoon | | 606/151 |
| 5,843,126 A * | 12/1998 | Jameel | | 606/220 |
| 6,869,436 B2 * | 3/2005 | Wendlandt | | 606/151 |
| 7,481,832 B1 * | 1/2009 | Meridew et al. | | 606/319 |
| 8,043,331 B2 * | 10/2011 | Pugsley et al. | | 606/220 |
| 2003/0065340 A1 * | 4/2003 | Geitz | | 606/151 |
| 2003/0149439 A1 | 8/2003 | Wendlandt | | |
| 2004/0167572 A1 | 8/2004 | Roth et al. | | |
| 2008/0114383 A1 * | 5/2008 | Hunt et al. | | 606/153 |
| 2008/0140095 A1 * | 6/2008 | Smith et al. | | 606/151 |
| 2008/0149685 A1 * | 6/2008 | Smith et al. | | 227/181.1 |
| 2008/0281354 A1 * | 11/2008 | Cropper et al. | | 606/220 |
| 2009/0192554 A1 | 7/2009 | Bennett | | |

OTHER PUBLICATIONS

European Search Report dated Sep. 5, 2013 from European Application No. EP10251455.1 (7 pgs.).

* cited by examiner

*Primary Examiner* — Corrine M McDermott
*Assistant Examiner* — Mark Mashack

(57) ABSTRACT

A ligation device is disclosed that is capable of containing a fluid, e.g., a biomechanical medium or an antimicrobial solution. The ligation device comprises an upper clip and a lower clip, each having a locking feature that enables the upper clip and the lower clip to be movably attached to each other.

10 Claims, 2 Drawing Sheets

LOCAL BIOMECHANICAL AND/OR ANTIMICROBIAL LIGATION DEVICE

BACKGROUND

1. Technical Field

The present disclosure relates to apparatus and methods for joining tissue portions and occluding vessels.

2. Background of Related Art

Ligation devices are used to join tissue portions and to occlude vessels. When tissue is held together by ligation devices that penetrate the body, the risk of foreign matter entering the site of a surgical wound is increased. To reduce the risk of infection, ligation devices can be coated with an antimicrobial or antibiotic material.

Once inserted into the body, ligation devices will remain in place unless they are either physically removed or dissolved in the body. The physical removal of non-resorbable ligation devices is a complicated surgical procedure typically involving the use of specially designed instruments.

SUMMARY

The present disclosure describes various methods and devices for tissue ligation and/or vessel occlusion. A device for delivering a localized antimicrobial solution or a biomechanical medium is described.

A ligation device may include a fastener member having a backspan and at least two prongs generally perpendicular to the backspan, a retainer portion having a connector and at least two columnar members attached to the connector, each columnar member having an aperture to receive and to retain the prongs, and a reservoir located within at least one of the columnar members. In another embodiment, the ligation device may include a fastener member having a backspan and legs generally perpendicular to the backspan with at least one leg housing a reservoir, and a retainer portion with a connector and at least two columnar members attached to the connector, each columnar member having an aperture to receive and retain the legs. The ligation device may also include a locking surface extending from at least one prong that is removably attached to a locking surface extending from at least one aperture.

Within the reservoir, a fluid such as an antimicrobial medium or solution may be stored. To facilitate storage of the fluid, a membrane seal may be positioned at the opening of the reservoir. Dispersion of the fluid may be facilitated by puncturing the membrane seal upon insertion of the fastener member into the retainer portion. The prongs of the fastener member may include a sharp distal tip to facilitate the opening of the membrane seal. A groove may be located on an inner surface of the retainer portion to facilitate dispersion of the fluid.

The various aspects of the present disclosure will be more readily understood from the following description when read in conjunction with the appended figures.

BRIEF DESCRIPTION OF THE DRAWINGS

By way of description only, embodiments of the disclosure will be described with reference to the accompanying drawings, in which.

DETAILED DESCRIPTION

Figure 2:
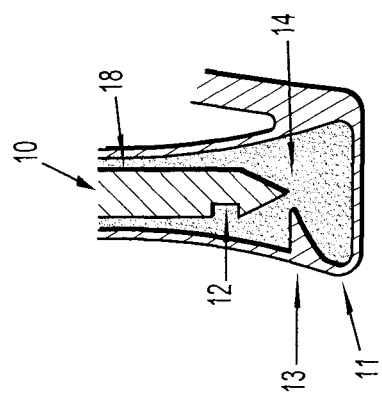
FIG. 2 is a side cross-sectional view of the ligation device of FIG. 1 showing a distal portion of an upper clip inserted into a cavity of a lower leg.

Particular embodiments of the present disclosure will be described herein with reference to the accompanying drawings. As shown in the drawings and as described throughout the following descriptions, and is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

Figure 1:
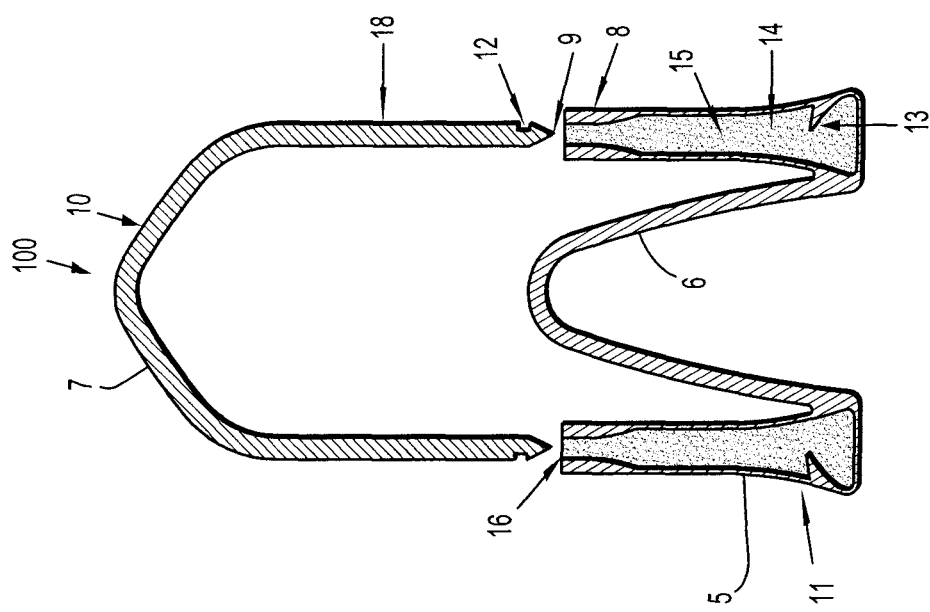
FIG. 1 is a side cross-sectional view showing a ligation device according to one embodiment of the present disclosure.

As seen in FIG. 1, a ligation device 100 is shown including a fastener member 10 and a retainer portion 11. The fastener member 10 includes a backspan 7 and at least two prongs or legs 18 that are generally perpendicular to the backspan 7. The retainer portion 11 includes a connector 6 and at least two columnar members 5 configured and adapted to receive the prongs 18 of the fastener member 10 therein. The connector 6 is a generally U-shaped member. The connector 6 may be resilient or flexible. As such, the connector 6 allows the columnar members 5 to move towards each other and away from each other. Similarly, the backspan 7 may be resilient or flexible, thereby allowing the fastener member 10 to match the spacing between the columnar members 5 of the retainer portion 11. At least one of the columnar members 5 is configured and adapted to store a fluid 15 within a reservoir 14 within the columnar member 6. A membrane seal 16 may be positioned on or within the retainer portion 11 to facilitate storage of the fluid 15 within the reservoir 14. The fluid 15 is released from the reservoir 14 upon insertion of the fastener member 10 into the retainer portion 11. To facilitate release of the fluid 15 upon insertion of the fastener member 10 into the retainer portion 11, prongs 18 may include a sharp distal tip 9 that is configured and adapted to puncture the membrane seal 16. Dispersion of the fluid 15 may be facilitated by a groove 8, as shown in FIG. 1, positioned on the inner profile of the retainer portion 11. In an alternative embodiment, the groove 8 may be positioned on the inner profile of the fastener member 10.

Figure 3:
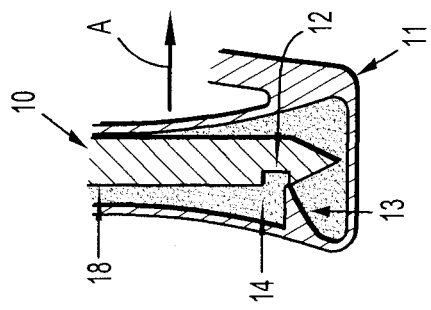
FIG. 3 is a side cross-sectional view of the ligation device of FIG. 2 showing the upper leg engaged in the cavity of the lower leg.

As seen in FIGS. 1-3, prong 18 is shown having a recess 12 that is engagable with a protrusion 13 within the columnar member 8. Variations of this structure that are in the spirit of this disclosure will be apparent to those skilled in the art. For example, the prong 18 may have a protrusion that is engagable with a recess within the columnar member 8. FIG. 3 shows the recess 12 engaged with the protrusion 13, thereby locking the fastener member 10 to the retainer portion 11. As shown in FIG. 3, the recess 12 can be disengaged form the protrusion 13 by sliding the retainer portion 11 apart from the fastener member 10 in the direction of arrow A. To facilitate movement of the fastener member 10 and the retainer portion 11 apart from each other, the fastener member 10 and the retainer portion 11 may be formed from a material capable or small defections, e.g., an elastic and/or resilient material.

Figure 4:
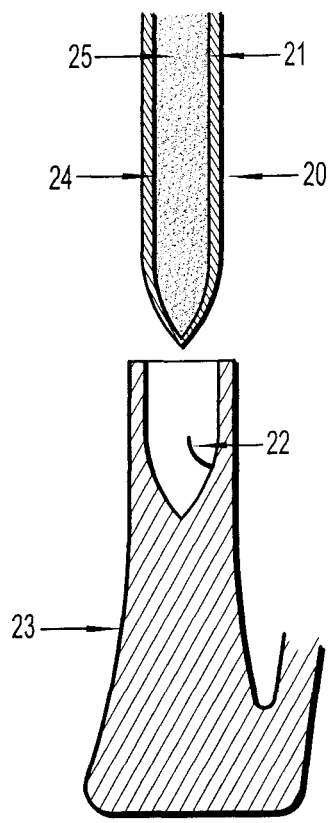
FIG. 4 is a front view of a ligation device according to an embodiment of the present disclosure.

In an alternative embodiment, as seen in FIG. 4, ligation device 200 includes an upper clip 20 and a lower clip 23. The upper clip 20 includes a leg 20a including a reservoir 24 that is sealed by a membrane 21. The lower clip 23 includes a cutting element 22 extending from columnar member 23a that is capable of puncturing the membrane 21. Fluid 15 can be stored within the reservoir 24.

Fluid 15 may be for example, but is not limited to being, an antiseptic or an antimicrobial solution, a biomechanical medium, and/or a wound treatment material. Examples of antimicrobial agents include but are not limited to β-Lactam agents, such as penicillins, and cephalosporins. By way of example only, the fluid 15 may include an antimicrobial hydrogel and may be in the form of a thixotropic, non-cytotoxic hydrogel. Preferably, the fluid 15 will facilitate healing by decreasing the likelihood of infection while not inhibiting healing of the surgical site.

The ligation devices disclosed herein may be made from natural or synthetic bioabsorbable materials, including but not limited to, alloys and polymers. Examples of families of bioabsorbable polymers include polymers having glycolic and ester linkages, including but not limited to polyesters, poly (amino acids), polyanhydrides, polyortho-esters, polyurethanes, polycarbonates, poly(dioxanone) (PDO), polyethylene glycol (hydrogels, polylactides (PLA), polyglycolides (PGA), polycaprolactone (PCL), and their copolymers. Some of the polymers, such as hydrogels, are hydrophilic. Others, such as PCL, are hydrophobic. The bioabsorbable polymers may be prepared by copolymerization of various monomers to modify and improve their properties as applications demand, e.g., poly (lactide-co-glycolide) copolymers. Because these polymers degrade by hydrolysis, the type of polymer and its physical form used in a particular application has an effect in defining the degradation period. Mechanical blending, as opposed to copolymerization, can also further enhance their properties.

Biocompatible, solid-solution strengthened alloys such as iron-based alloys, cobalt-based alloys and titanium-based alloys as well as refractory metals and refractory-based alloys may be utilized in the manufacture of such implantable medical devices. For example, traditional stainless steel alloys such as 316L, i.e., UNS S31603, may be utilized as an implantable, biocompatible device material. Depending upon the material selected, degradation of the material may be accelerated after exposing the material to radiation, including but not limited to gamma radiation.

Additionally, the ligation device 100 may also be made from materials impregnated or coated with substances known to have antimicrobial properties, such as silver or an antimicrobial medium. For example, oligodynamic metals including silver, copper, iron, zinc, bismuth, gold, aluminum, and other metals are known to have antimicrobial properties.

It will be understood by those skilled in the art that various modifications and changes in form and detail may be made therein without departing from the scope and spirit of the present disclosure. Accordingly, modifications such as those suggested above, but not limited thereto, are to be considered within the scope of the disclosure.

What is claimed is:

1. A ligation device comprising:
   a fastener member having a backspan and at least two prongs generally perpendicular to the backspan;
   a retainer portion having a connector and at least two columnar members attached to the connector, each columnar member having an aperture to receive and to retain the prongs; and
   a reservoir defining a container configured to store a fluid therein, the reservoir located within at least one of the columnar members, the fastener member releasably secured to the retainer portion, wherein the fastener member is releasable from the retainer portion upon flexing of the at least two prongs toward each other, wherein the retainer portion is flexible such that the at least two columnar members are movable toward and away from each other.

2. The ligation device of claim 1 further comprising: a locking surface extending from at least one prong that is removably attached to a locking surface extending from at least one aperture.

3. The ligation device of claim 2, wherein each prong defines a distal end that is disposed within the respective columnar member when the fastener member is releasably secured to the retainer portion.

4. The ligation device of claim 1 further comprising a membrane seal at an opening of the aperture.

5. The ligation device of claim 1, wherein the prongs have a sharp distal tip.

6. The ligation device of claim 1, wherein the fluid is either an antimicrobial solution or a biomechanical medium.

7. The ligation device of claim 1, further comprising a groove located on the inner surface of the retainer portion.

8. The ligation device of claim 1, wherein at least one of the at least two prongs includes a groove and the retainer portion includes a protrusion configured to releasably engage the groove.

9. The ligation device of claim 8, wherein the fastener member is separable from the retainer member when the groove is separated from the protrusion of the retainer portion.

10. The ligation device of claim 1, wherein the retainer portion defines a gap between the at least two columnar members.

* * * * *